United States Patent
Maruyama

(10) Patent No.: US 11,154,473 B2
(45) Date of Patent: Oct. 26, 2021

(54) COMPOSITION COMPRISING RESORCINOL OR DERIVATIVE THEREOF

(71) Applicant: L'OREAL, Paris (FR)

(72) Inventor: Kazuhiko Maruyama, Kawasaki (JP)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/474,439

(22) PCT Filed: Jan. 12, 2018

(86) PCT No.: PCT/JP2018/001469
§ 371 (c)(1),
(2) Date: Jun. 27, 2019

(87) PCT Pub. No.: WO2018/159139
PCT Pub. Date: Sep. 7, 2018

(65) Prior Publication Data
US 2019/0336421 A1  Nov. 7, 2019

(30) Foreign Application Priority Data

Feb. 28, 2017 (JP) .............................. JP2017-036113

(51) Int. Cl.
| | | |
|---|---|---|
| *A61Q 19/02* | (2006.01) | |
| *A61K 8/34* | (2006.01) | |
| *A61K 8/37* | (2006.01) | |
| *A61K 8/42* | (2006.01) | |
| *A61K 8/49* | (2006.01) | |
| *A61K 8/58* | (2006.01) | |

(52) U.S. Cl.
CPC ............... *A61K 8/347* (2013.01); *A61K 8/37* (2013.01); *A61K 8/42* (2013.01); *A61K 8/4913* (2013.01); *A61K 8/4966* (2013.01); *A61K 8/585* (2013.01); *A61Q 19/02* (2013.01)

(58) Field of Classification Search
None
See application file for complete search history.

(56) References Cited

U.S. PATENT DOCUMENTS

| | | | |
|---|---|---|---|
| 2008/0305059 A1 | 12/2008 | Chaudhuri | |
| 2011/0033512 A1* | 2/2011 | Breyfogle | A61K 8/895 424/401 |
| 2011/0213030 A1 | 9/2011 | Shinto et al. | |
| 2013/0281507 A1 | 10/2013 | Marat | |

FOREIGN PATENT DOCUMENTS

| | | |
|---|---|---|
| CN | 101084862 A | 12/2007 |
| CN | 104414869 A | 3/2015 |
| JP | 2002-285019 A | 10/2002 |
| JP | 2009-242321 A | 10/2009 |
| JP | 2009-286735 A | 12/2009 |
| WO | 03/080009 A1 | 10/2003 |
| WO | 2010/078985 A2 | 7/2010 |
| WO | 2018/001485 A1 | 1/2018 |

OTHER PUBLICATIONS

ISA/EP, PCT International Search Report dated Apr. 26, 2018, which was issued in connection with PCT Application No. PCT/JP2018/001469 (4 pages).
JPO, Office Action for the corresponding Japanese application No. 2017-036113, dated Apr. 5, 2021, with English translation.
CNIPA, Office Action for the corresponding Chinese application No. 201880008754.8, dated Aug. 24, 2021, with English translation.

\* cited by examiner

*Primary Examiner* — Jyothsna A Venkat
(74) *Attorney, Agent, or Firm* — Lucas & Mercanti, LLP

(57) ABSTRACT

The present invention relates to a composition, preferably a cosmetic composition, comprising: (a) at least one compound selected from the group consisting of resorcinol and resorcinol derivatives; (b) at least one lipophilic UV filter; (c) at least one lipophilic antioxidant; and (d) at least one oil. The composition according to one embodiment of the present invention is stable with regard to light and/or temperature.

3 Claims, No Drawings

COMPOSITION COMPRISING RESORCINOL OR DERIVATIVE THEREOF

CROSS-REFERENCE TO RELATED APPLICATIONS

This application is a 371 of PCT/JP2018/001469, filed on Jan. 12, 2018, which claims benefit of Japanese Patent Application No. 2017-036113 filed on Feb. 28, 2017, each of which is hereby incorporated by reference in its entirety.

TECHNICAL FIELD

The present invention relates to a composition comprising resorcinol or a derivative thereof.

BACKGROUND ART

Resorcinol and derivatives thereof are known to have a melanin protection inhibitory effect, and therefore, are often incorporated into cosmetics for the purpose of skin whitening.

JP-A-2009-242321 discloses a dermatological composition including an alkylresorcinol and an antioxidant selected from sulfur-containing compounds, alpha-tocopherol and derivatives thereof, and butylhydroxytoluene.

JP-A-2009-286735 discloses a dermatological composition including an alkylresorcinol, L-ascorbic acid derivative, and a compound selected from sterol-structure compounds, Vitamin E derivatives, sorbitan-structure compounds and the like.

WO 03/080009 discloses a personal care composition including an organic sunscreen and a resorcinol derivative.

DISCLOSURE OF INVENTION

However, compositions including resorcinol and derivatives thereof have a problem in that they tend to become unstable due to light and/or depending on temperature. For example, the compositions tend to change in color and/or have odor and/or cause precipitations, due to exposure to light and/or under relatively high temperatures. However, sufficient investigations have not as yet been made for the technique of effectively preventing the destabilization of compositions including resorcinol or derivatives thereof.

An objective of the present invention is to provide a composition including resorcinol or derivatives thereof which is stable under the influence of light and/or temperature.

The above objective of the present invention can be achieved by a composition, preferably a cosmetic composition, comprising:
(a) at least one compound selected from the group consisting of resorcinol and resorcinol derivatives;
(b) at least one lipophilic UV filter;
(c) at least one lipophilic antioxidant; and
(d) at least one oil.

The resorcinol derivative may be a compound represented by formula (I):

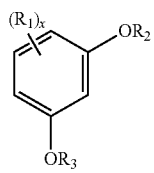
(I)

wherein
$R_1$ independently denotes -A-B where A represents a single bond, a $C_1$-$C_6$ alkylene group, a $C_6$-$C_{12}$ arylene group, or a $C_1$-$C_6$ alkylene-$C_6$-$C_{12}$ arylene group, and B represents a halogen atom, —OH, —COH, —COOH, —CONH$_2$, —NH$_2$, a $C_1$-$C_6$ alkyl group, a $C_1$-$C_6$ alkoxy group, a $C_1$-$C_6$ acyl group, a carbocyclic group, preferably an aryl group, or heterocyclic group, preferably a non-aromatic heterocyclic group, each of which may be substituted with at least one substituent selected from the group consisting of a hydroxyl group, a carboxyl group, a $C_1$-$C_6$ alkyl group, a $C_1$-$C_6$ alkylene-OH, an amino group, —CONH$_2$, —CONH—$C_1$-$C_6$ alkyl group and a $C_1$-$C_6$ alkoxy group;

x is an integer of 1 to 4; and $R_2$ and $R_3$ independently denote a hydrogen atom, a $C_1$-$C_6$ alkyl group, or a $C_1$-$C_6$ acyl group, or a salt, a solvate, an optical isomer thereof, or a racemate thereof.

In particular, the resorcinol derivative may be a compound represented by formula (Ia):

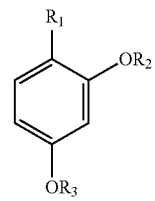
(Ia)

wherein
$R_1$, $R_2$ and $R_3$ have the same meanings as above, or a salt, a solvate, an optical isomer thereof, or a racemate thereof.

In formula (Ia), it may be preferable that
$R^1$ denotes -A-B where A represents a single bond or a $C_1$-$C_6$ alkylene group, and B represents a phenyl group or a tetrahydropyranyl group; and each of $R_2$ and $R_3$ denotes a hydrogen atom.

Alternatively, the resorcinol derivative may be a compound represented by formula (II):

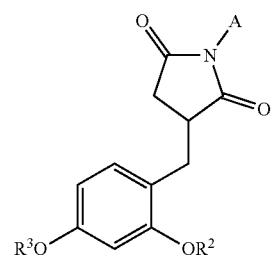
(II)

wherein
$R_2$ and $R_3$ independently denote a hydrogen atom or an acetyl group;

A denotes a radical selected from:
a) —H;
b) -a $C_3$-$C_8$ cyclic or $C_3$-$C_{20}$ branched or $C_2$-$C_{20}$ unsaturated or $C_1$-$C_{20}$ saturated linear alkyl group which is optionally interrupted by one or more heteroatoms or moieties selected from N, O and —CO— or a combination thereof such as —NHCO—, —NHCONH— and/or is optionally substituted by one or more identical or different groups selected from:
i) —OR$_5$
ii) —SR$_5$
iii) —NR$_6$R$_7$
iv) —CONHR$_6$
v) —CONR$_6$R$_7$
vi) —COOR$_6$
vii) —NCONHR$_6$
viii) —C(O)C$_1$-C$_4$ alkyl
ix) a C$_5$-C$_{12}$ (hetero)aryl group optionally containing one or more heteroatoms selected from O, N and S and optionally substituted by one or more hydroxyls and/or by one or more C$_1$-C$_8$ alkoxy radicals;
x) a saturated or unsaturated, non-aromatic heterocycle having from 5 to 8 members and comprising one or more heteroatoms selected from O, N and S which is optionally substituted by one or more hydroxyls and/or by one or more C$_1$-C$_8$ alkoxy or C$_1$-C$_4$ alkyl radicals, it being possible for one of the members to be a carbonyl group;

c) -a C$_5$-C$_{12}$ (hetero)aryl group optionally containing one or more heteroatoms selected from O, N and S and optionally substituted by one or more hydroxyls and/or by one or more radicals selected from C$_1$-C$_8$ alkoxy or C$_1$-C$_8$ alkyl groups;
d) —NR$_8$R$_9$;
e) —OR$_4$;
f) —C(O)NHR$_4$;
g) C(O)C$_1$-C$_{10}$ alkyl,
where
R$_8$ and R$_9$, which are identical or different, denote a radical selected from:
a) —H;
b) -a C$_3$-C$_8$ cyclic or C$_3$-C$_{10}$ branched or C$_2$-C$_{10}$ unsaturated or C$_1$-C$_{10}$ linear saturated alkyl group which is optionally interrupted by one or more heteroatoms or moieties selected from N, O and —CO— or a combination thereof such as —NHCO—, —NHCONH— and/or is optionally substituted by one or more identical or different groups selected from —OR$_5$;
c) a C$_5$-C$_{12}$ (hetero)aryl group optionally containing one or more heteroatoms selected from O, N and S and optionally substituted by one or more hydroxyls and/or by one or more C$_1$-C$_8$ alkoxy radicals;

it being possible for R$_8$ and R$_9$ to form, with the nitrogen which carries them, a heterocycle which has from 5 to 8 members and may contain one or more heteroatoms or moieties selected from N, O and —CO— and/or is optionally substituted by a C$_1$-C$_{10}$ hydrocarbon chain optionally containing one or more radicals selected from hydroxyl or C$_1$-C$_4$ alkoxy; R$_4$ denotes a radical selected from:
a) —H
b) a C$_3$-C$_8$ cyclic or C$_3$-C$_{10}$ branched or C$_1$-C$_{10}$ linear saturated alkyl group which is optionally substituted by one or more identical or different groups selected from:
i) —COOR$_6$,
ii) a C$_5$-C$_{12}$ (hetero)aryl radical which optionally contains one or more heteroatoms selected from O, N and S and is optionally substituted by one or more hydroxyls and/or by one or more C$_1$-C$_8$ alkoxy radicals;
c) a C$_5$-C$_{12}$ (hetero)aryl group which optionally contains one or more heteroatoms selected from O, N and S and is optionally substituted by one or more hydroxyls and/or by one or more C$_1$-C$_5$ alkoxy radicals;

R$_5$ is selected from H and a C$_3$-C$_8$ cyclic or C$_2$-C$_{10}$ unsaturated or C$_3$-C$_{10}$ branched or C$_1$-C$_{10}$ linear saturated alkyl hydrocarbon group;

R$_6$ and R$_7$, which are identical or different, are selected from H, a C$_3$-C$_8$ cyclic or C$_2$-C$_{10}$ unsaturated or C$_3$-C$_{13}$ branched or C$_1$-C$_{10}$ linear saturated alkyl hydrocarbon group; a (C$_1$-C$_4$)alkyl-C$_6$ (hetero)aryl group optionally containing a nitrogen atom, more particularly a benzyl group;

R$_6$ and R$_7$ may form, with the nitrogen which carries them, a heterocycle which has from 5 to 8 members and may contain one or more heteroatoms or moieties selected from N, O and —CO— and/or is optionally substituted by a C$_1$-C$_{10}$ hydrocarbon chain;

h) a radical of formula (III):

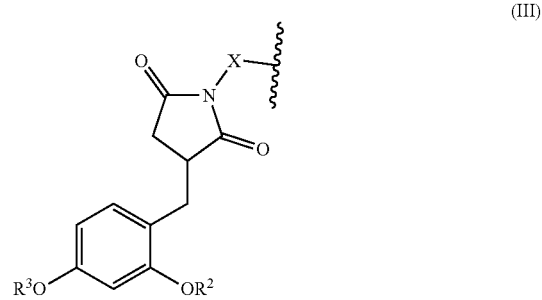

(III)

in which:
X denotes C$_3$-C$_8$ cyclic or C$_3$-C$_{10}$ branched or C$_1$-C$_{10}$ linear saturated hydrocarbon chain or a C$_6$-C$_{12}$ arylene group such as phenylene, or a C$_1$-C$_4$ alkylene-C$_6$-C$_8$ cycloalkylene-C$_1$-C$_4$ alkylene group or a C$_1$-C$_4$ alkylene-phenylene-C$_1$-C$_4$ alkylene group, which is optionally substituted by one or more identical or different radicals selected from —OH, —COOR$_6$ where R$_6$ denotes H or a C$_3$-C$_8$ cyclic or C$_2$-C$_{10}$ unsaturated or C$_3$-C$_{10}$ branched or C$_1$-C$_{20}$ linear saturated alkyl hydrocarbon group;

R$_2$ and R$_3$ have the same meanings as above; and when A denotes a radical of formula (III), all of the radicals R$_2$ and r$_3$ in the compounds of formula (II) are identical, or a salt, a solvate, an optical isomer thereof, or a racemate thereof.

It may be preferable that R$_2$ and R$_3$ denote a hydrogen atom, and A denotes a C$_3$-C$_{10}$ branched or C$_1$-C$_{10}$ linear saturated alkyl group.

The amount of ingredient (a) may range from 0.01 to 25% by weight, preferably from 0.1 to 20% by weight, and more preferably from 0.2 to 15% by weight, relative to the total weight of the composition.

The (b) lipophilic UV filter may be selected from the group consisting of butylmethoxydibenzoylmethane, ethylhexyl methoxycinnamate, ethylhexyl salicylate, homosalate, butylmethoxydibenzoylmethane, octocrylene, benzophenone-3, n-hexyl 2-(4-diethylamino-2-hydroxybenzoyl)benzoate, 4-methylbenzylidenecamphor, bis(ethylhexyloxyphenol)methoxyphenyltriazine, ethylhexyl triazone, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis(dineopentyl 4'-aminobenzalmalonate)-6-(n-butyl 4'-aminobenzoate)-s-triazine, 2,4,6-tris(biphenyl-4-yl)-1,3,5-triazine, 2,4,6-tris (terphenyl)-1,3,5-triazine, drometrizole trisiloxane, polysilicone-15,1,1-dicarboxy(2,2'-dimethylpropyl)-4,4-diphenylbutadiene, 2,4-bis[4-[5-(1,1-dimethylpropyl)

benzoxazol-2-yl]phenylimino]-6-[(2-ethylhexyl)imino]-1,3,5-triazine, and mixtures thereof.

The amount of ingredient (b) may range from 0.01 to 25% by weight, preferably from 0.1 to 20% by weight, and more preferably from 1 to 15% by weight, relative to the total weight of the composition.

The (c) lipophilic antioxidant agent may be selected from the group consisting of pentaerythrityl tetra-di-t-butyl hydroxyhydrocinnamate, nordihydroguaiaretic acid, ferulic acid, resveratrol, propyl gallate, butylated hydroxytoluene, butylated hydroxyanisole, ascorbyl palmitate, tocopherol, and mixtures thereof.

The amount of ingredient (c) may range from 0.01 to 20% by weight, preferably from 0.05 to 15% by weight, and more preferably from 0.1 to 10% by weight, relative to the total weight of the composition.

The (d) oil may be selected from polar oils, preferably ester oils.

The amount of ingredient (d) may range from 50 to 95% by weight, preferably from 60 to 93% by weight, and more preferably from 70 to 90% by weight, relative to the total weight of the composition.

The composition according to the present invention may be anhydrous.

Furthermore, the present invention also relates to a cosmetic process for a keratin substance, comprising applying the composition according to the present invention onto the keratin substance.

BEST MODE FOR CARRYING OUT THE INVENTION

After diligent research, the inventors have discovered that it is possible to provide a composition including resorcinol or derivatives thereof which is stable under the influence of light and/or temperature.

Thus, one aspect of the present invention is a composition, comprising:
(a) at least one compound selected from the group consisting of resorcinol and resorcinol derivatives;
(b) at least one lipophilic UV filter;
(c) at least one lipophilic antioxidant; and
(d) at least one oil.

The composition according to the present invention is stable with regard to light and/or temperature. For example, the composition according to the present invention does not tend to change in color and/or have odor and/or cause precipitations, due to exposure to light and/or under relatively high temperatures, although it includes resorcinol or derivatives thereof. The composition according to the present invention can be stable over time even under exposure to light and/or under relatively high temperatures.

Thus, the composition according to the present invention is preferable as a cosmetic composition.

Hereinafter, the composition according to the present invention will be explained in a more detailed manner.

[Resorcinol or Resorcinol Derivative]

The composition according to the present invention comprises (a) at least one compound selected from the group consisting of resorcinol and resorcinol derivatives. A single type of resorcinol derivative may also be used, but two or more different types of resorcinol derivative may be used in combination. A combination of resorcinol and a resorcinol derivative or a combination of different resorcinol compounds may be used.

In one embodiment, the resorcinol derivative may be a compound represented by formula (I):

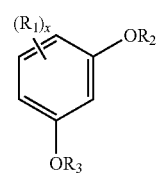

wherein $R_1$ independently denotes -A-B where A represents a single bond, a $C_1$-$C_6$ alkylene group, a $C_6$-$C_{12}$ arylene group, or a $C_1$-$C_6$ alkylene-$C_6$-$C_{12}$ arylene group, and B represents a halogen atom, —OH, —COH, —COOH, —CONH$_2$, —NH$_2$, a $C_1$-$C_6$ alkyl group, a $C_1$-$C_6$ alkoxy group, a $C_1$-$C_6$ acyl group, a carbocyclic group, preferably an aryl group, or heterocyclic group, preferably a non-aromatic heterocyclic group, each of which may be substituted with at least one substituent selected from the group consisting of a hydroxyl group, a carboxyl group, a $C_1$-$C_6$ alkyl group, a $C_1$-$C_6$ alkylene-OH, an amino group, —CONH$_2$, —CONH—$C_{1-6}$ alkyl group and a $C_1$-$C_6$ alkoxy group;

x is an integer of 1 to 4, preferably 1 to 3, more preferably 1 or 2 and even more preferably 1; and $R_2$ and $R_3$ independently denote a hydrogen atom, a $C_1$-$C_6$ alkyl group, or a $C_1$-$C_6$ acyl group, or a salt, a solvate, an optical isomer thereof, or a racemate thereof.

The $C_1$-$C_6$ alkylene group may be a straight or branched divalent group.

The $C_1$-$C_6$ alkylene-$C_6$-$C_{12}$ arylene group may also be a straight or branched divalent group. Either the $C_1$-$C_6$ alkylene moiety or the $C_6$-$C_{12}$ arylene moiety may bond the dihydroxy benzene ring shown in formula (I).

The aryl group as "B" may be a $C_6$-$C_{12}$ aryl group such as a phenyl group, a tolyl group and a xylyl group, or a naphthyl group.

The hetero atom in the heterocyclic group as "B" may be an oxygen atom, a sulfur atom and a nitrogen atom. A single heteroatom or a plurality of hetero atoms may be included in the heterocyclic group. As examples of the heterocyclic group, mention may be made of a furanyl group, a pyrrole group, an oxazole group, an isoxazolyl group, a thiazolyl group, an isothiazolyl group, an imidazolyl group, a pyrazolyl group, a pyranyl group, a pyridinyl group, a pyridazinyl group, a pyrimidinyl group, a pyrazinyl group, an indolyl group, an isoindolyl group, a benzofuranyl group, a quinolinyl group, isoquinolinyl group and an indazolyl group.

As examples of the non-aromatic heterocyclic group, mention may be made of a pyrrolidinyl group, an imidazolidinyl group, a pyrazolidinyl group, a piperidinyl group, a piperazinyl group, a morpholinyl group, and a tetrahydropyranyl group.

As examples of the compound according to formula (I), mention may be made of: phenylethyl resorcinol, 2-methylresorcinol, 5-methylresorcinol, 4-methylresorcinol, 2,4-dihydroxybenzaldehyde, 4-ethylresorcinol, 2,5-dimethylresorcinol, 4,5-dimethylresorcinol, 2,4-dimethyl-1,3-benzenediol, 3,5-dihydroxybenzylamine, 5-methoxyresorcinol, 3,5-dihydroxybenzyl alcohol, 2-methoxyresorcinol, 4-methoxyresorcinol, 3,5-dihydroxytoluene monohydrate, 4-chlororesorcinol, 2-chlororesorcinol, 2',4'-dihydroxyacetophenone, 3',5'-dihydroxyacetophenone, 2,6-dihydroxy-4-methylbenzaldehyde, 4-propylresorcinol, 2,4-dihydroxy-1,3,5-trimethylbenzene, 3,5-dihydroxybenzamide, 2,6-dihydroxybenzamide, 2,4-dihydroxybenzamide, 2,4-dihydroxybenzoic acid, 2,6-dihydroxybenzoic acid, 3,5-dihydroxybenzoic acid, 2,6-dihydroxy-4-methylbenzyl alcohol, 3,5-dihydroxyanisole hydrate, 4-aminoresorcinol hydrochloride, 2-aminoresorcinol hydrochloride, 5-aminobenzene-1,3-diol hydrochloride, 2',4'-dihydroxypropiophenone, 2',4'-dihydroxy-3'-methylacetophenone, (2,4-dihydroxyphenyl)acetone, (3,5-dihydroxyphenyl)acetone, 2,6-dihydroxy-4'-methylacetophenone, 4-n-butylresorcinol, 2,4-diethyl-1,3-benzenediol, 3,5-dihydroxy-4-methylbenzoic acid, 2,6-dihydroxy-4-methylbenzoic acid, 2,4-dihydroxy-6-methylbenzoic acid, 3,5-dihydroxyphenylacetic acid, 2-ethyl-5-methoxybenzene-1,3-diol, 4-amino-3,5-dihydroxybenzoic acid, 3,5-dihydroxyacetophenone monohydrate, 3,5-dihydroxybenzylamine hydrochloride, 4,6-dichlororesorcinol, 2',4'-dihydroxy-3'-methylpropiophenone, 1-(3-ethyl-2,6-dihydroxyphenyl)ethan-1-one, 2',6'-dihydroxy-4'-methoxyacetophenone, 1-(2,6-dihydroxy-3-methoxyphenyl)ethan-1-one, 3(2,4-dihydroxyphenylpropionic acid, 2,4-dihydroxy-3,6-dimethylbenzoic acid, and hexylresorcinol It is preferable that the resorcinol derivative be a compound represented by formula (Ia):

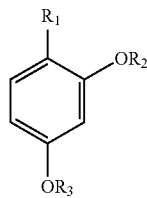

(Ia)

wherein $R_1$, $R_2$ and $R_3$ have the same meanings as above, or a salt, a solvate, an optical isomer thereof, or a racemate thereof.

It is more preferable that, in the above formula (Ia), $R^1$ denotes -A-B where A represents a single bond or a $C_1$-$C_6$ alkylene group, and B represents a phenyl group or a tetrahydropyranyl group; and each of $R_2$ and $R_3$ denotes a hydrogen atom.

It is even more preferable that the resorcinol derivative be phenylethyl resorcinol.

It is also preferable that the resorcinol derivative be a compound represented by formula (II):

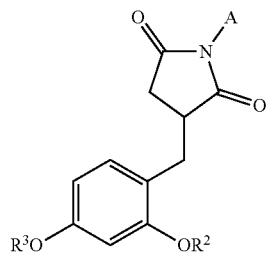

(II)

wherein $R_2$ and $R_3$ independently denote a hydrogen atom or an acetyl group;

A denotes a radical selected from:
a) —H;
b) -a $C_3$-$C_8$ cyclic or $C_3$-$C_{20}$ branched or $C_2$-$C_{20}$ unsaturated or $C_1$-$C_{20}$ saturated linear alkyl group which is optionally interrupted by one or more heteroatoms or moieties selected from N, O and —CO— or a combination thereof such as —NHCO—, —NHCONH— and/or is optionally substituted by one or more identical or different groups selected from:
  i) —$OR_5$
  ii) —$SR_5$
  iii) —$NR_6R_7$
  iv) —$CONR_6$
  v) —$CONR_6R_7$
  vi) —$COOR_6$
  vii) —$NHCONHR_6$
  viii) —$C(O)C_1$-$C_4$ alkyl
  ix) a $C_5$-$C_{12}$ (hetero)aryl group optionally containing one or more heteroatoms selected from O, N and S and optionally substituted by one or more hydroxyls and/or by one or more $C_1$-$C_8$ alkoxy radicals;
  x) a saturated or unsaturated, non-aromatic heterocycle having from 5 to 8 members and comprising one or more heteroatoms selected from O, N and S which is optionally substituted by one or more hydroxyls and/or by one or more $C_1$-$C_8$ alkoxy or $C_1$-$C_4$ alkyl radicals, it being possible for one of the members to be a carbonyl group;
c) -a $C_5$-$C_{12}$ (hetero)aryl group optionally containing one or more heteroatoms selected from O, N and S and optionally substituted by one or more hydroxyls and/or by one or more radicals selected from $C_1$-$C_8$ alkoxy or $C_1$-$C_8$ alkyl groups;
d) —$NR_8R_9$;
e) —$OR_4$;
f) —$C(O)NHR_4$;
g) $C(O)C_1$-$C_{10}$ alkyl,
where $R_8$ and $R_9$, which are identical or different, denote a radical selected from:
a) —H;
b) -a $C_3$-$C_8$ cyclic or $C_3$-$C_{10}$ branched or $C_2$-$C_{10}$ unsaturated or $C_1$-$C_{10}$ linear saturated alkyl group which is optionally interrupted by one or more heteroatoms or moieties selected from N, O and —CO— or a combination thereof such as —NHCO—, —NHCONH— and/or is optionally substituted by one or more identical or different groups selected from —$OR_5$;
c) a $C_5$-$C_{12}$ (hetero)aryl group optionally containing one or more heteroatoms selected from O, N and S and optionally substituted by one or more hydroxyls and/or by one or more $C_1$-$C_8$ alkoxy radicals;

it being possible for $R_8$ and $R_9$ to form, with the nitrogen which carries them, a heterocycle which has from 5 to 8 members and may contain one or more heteroatoms or moieties selected from N, O and —CO— and/or is optionally substituted by a $C_1$-$C_{10}$ hydrocarbon chain optionally containing one or more radicals selected from hydroxyl or $C_1$-$C_4$ alkoxy;

$R_4$ denotes a radical selected from:
a) —H
b) a $C_3$-$C_8$ cyclic or $C_3$-$C_{10}$ branched or $C_1$-$C_{10}$ linear saturated alkyl group which is optionally substituted by one or more identical or different groups selected from:
  i) —$COOR_6$,
  ii) a $C_5$-$C_{12}$ (hetero)aryl radical which optionally contains one or more heteroatoms selected from O, N and S and is optionally substituted by one or more hydroxyls and/or by one or more $C_1$-$C_8$ alkoxy radicals;

c) a $C_5$-$C_{12}$ (hetero)aryl group which optionally contains one or more heteroatoms selected from O, N and S and is optionally substituted by one or more hydroxyls and/or by one or more $C_1$-$C_8$ alkoxy radicals;

$R_5$ is selected from H and a $C_3$-$C_8$ cyclic or $C_2$-$C_{10}$ unsaturated or $C_3$-$C_{10}$ branched or $C_1$-$C_{10}$ linear saturated alkyl hydrocarbon group;

$R_6$ and $R_7$, which are identical or different, are selected from H, a $C_3$-$C_8$ cyclic or $C_2$-$C_{10}$ unsaturated or $C_3$-$C_{10}$ branched or $C_1$-$C_{10}$ linear saturated alkyl hydrocarbon group; a ($C_1$-$C_4$)alkyl-$C_6$ (hetero)aryl group optionally containing a nitrogen atom, more particularly a benzyl group;

$R_6$ and $R_7$ may form, with the nitrogen which carries them, a heterocycle which has from 5 to 8 members and may contain one or more heteroatoms or moieties selected from N, O and —CO— and/or is optionally substituted by a $C_1$-$C_{10}$ hydrocarbon chain;

h) a radical of formula (III):

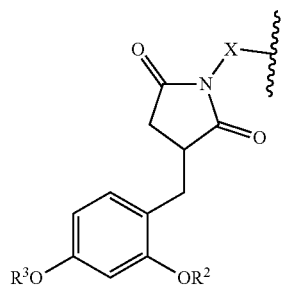

(III)

in which:

X denotes a $C_3$-$C_8$ cyclic or $C_3$-$C_{10}$ branched or $C_1$-$C_{10}$ linear saturated hydrocarbon chain or a $C_6$-$C_{12}$ arylene group such as phenylene, or a $C_1$-$C_4$ alkylene-$C_6$-$C_8$ cycloalkylene-$C_1$-$C_4$ alkylene group or a $C_1$-$C_4$ alkylene-phenylene-$C_1$-$C_4$ alkylene group, which is optionally substituted by one or more identical or different radicals selected from —OH, —COOR$_6$ where $R_6$ denotes H or a $C_3$-$C_8$ cyclic or $C_2$-$C_{10}$ unsaturated or $C_3$-$C_{10}$ branched or $C_1$-$C_{20}$ linear saturated alkyl hydrocarbon group;

$R_2$ and $R_3$ have the same meanings as above; and when A denotes a radical of formula (III), all of the radicals $R_2$ and $R_3$ in the compounds of formula (II) are identical, or a salt, a solvate, an optical isomer thereof, or a racemate thereof.

The salts of the compounds of formulae (I) and (II) include conventional non-toxic salts of said compounds, such as those formed from an acid or from a base.

Salts of the compound of formulae (I) and (II) (when it comprises a quaternizable nitrogen atom) include the following:

a) salts obtained by addition of compound (I) or (II) with a mineral acid, selected more particularly from hydrochloric, boric, hydrobromic, hydroic, sulphuric, nitric, carbonic, phosphoric and tetrafluoroboric acids;

b) or the salts obtained by addition of compound (I) or (II) with an organic acid, more particularly selected from acetic, propionic, succinic, fumaric, lactic, glycolic, citric, gluconic, salicylic, tartaric, terephthalic, methylsulphonic, ethylsulphonic, benzene sulphonic, toluene sulphonic and triflic acids.

Also included are the salts obtained by addition of the compound of formula (I) or (II) (when it comprises an acidic group) with a mineral base, such as aqueous sodium hydroxide and potassium hydroxide, calcium hydroxide, ammonium hydroxide, magnesium hydroxide, lithium hydroxide, and sodium, potassium or calcium carbonates or hydrogencarbonates, for example; or with an organic base such as a primary, secondary or tertiary alkylamine, for example triethylamine or butylamine. This primary, secondary or tertiary alkylamine may comprise one or more nitrogen and/or oxygen atoms and may therefore comprise, for example, one or more alcohol functions; included more particularly are 2-amino-2-methylpropanol, ethanolamine, triethanolamine, 2-dimethylamino propanol, 2-amino-2-(hydroxymethyl)-1,3-propanediol and 3-(dimethylamino)propylamine.

Also included are the salts of amino acids such as, for example, lysine, arginine, guanidine, glutamic acid and aspartic acid.

The salts of the compounds of formulae (I) and (II) (when they comprise an acidic group) may advantageously be selected from alkali metal salts or alkaline earth metal salts such as sodium, potassium, calcium and magnesium salts; and ammonium salts.

The salts of the compounds of formulae (I) and (II) (when they comprise a quaternizable nitrogen atom) may advantageously be selected from halides such as chloride and bromide; and from citrates, acetates, succinates, phosphates, lactates and tartrates.

The acceptable solvates of the compounds described in the present invention comprise conventional solvates such as those formed during the preparation of said compounds as a result of the presence of solvents. Examples include the solvates resulting from the presence of water or of linear or branched alcohols such as ethanol or isopropanol.

The optical isomers are more particularly enantiomers and diastereoisomers.

The linear or branched groups may preferably be selected from methyl, ethyl, propyl, isopropyl, butyl, isobutyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl and eicosyl.

The saturated linear or branched alkyl groups may more preferably be selected from methyl, ethyl, propyl, isopropyl, butyl, isobutyl, tert-butyl, pentyl, hexyl, heptyl and octyl.

The $C_1$-$C_4$ alkoxy groups may preferably be selected from methoxy, ethoxy, propoxy and butoxy and more preferably methoxy.

The compounds of formula (II) preferably have the following meanings:

$R_2$ and $R_3$ independently denote a hydrogen atom or an acetyl group;

A denotes a radical selected from:

a) —H b) -a $C_3$-$C_8$ cyclic or $C_3$-$C_{16}$ branched or $C_2$-$C_{16}$ unsaturated or $C_1$-$C_{16}$ linear saturated alkyl group which is optionally interrupted by one or more heteroatoms or moieties selected from N, O, —CO— and —NHC(O)— and/or is optionally substituted by one or more identical or different groups selected from:

i) —OH, ii) $C_1$-$C_4$ alkoxy, iii) —COOR$_6$, iv) —CONR$_6$R$_7$ where $R_6$ and $R_7$, which are identical or different, denote H or a $C_3$-$C_8$ cyclic or $C_2$-$C_8$ unsaturated or $C_3$-$C_8$ branched or $C_1$-$C_8$ linear saturated alkyl group;

v) a phenyl group which is optionally substituted by one or more hydroxyls and/or by one or more $C_1$-$C_4$ alkoxy radicals;

vi) a non-aromatic saturated or unsaturated heterocycle having from 5 to 8 members, comprising one or more heteroatoms selected from O, N and S, it being possible for one of the members to be a carbonyl group;

c) a $C_5$-$C_{12}$ aryl group such as phenyl which is optionally substituted by one or more identical or different radicals selected from OH, $C_1$-$C_4$ alkoxy and $C_1$-$C_4$ alkyl;

d) —$NR_8R_9$, where $R_8$ and $R_9$, which are identical or different, denote:

i) H;

ii) a $C_3$-$C_8$ cyclic or $C_2$-$C_8$ unsaturated or $C_3$-$C_8$ branched or $C_1$-$C_8$ linear saturated alkyl group which is optionally interrupted by an oxygen atom and/or is optionally substituted by a hydroxyl group or a $C_1$-$C_4$ alkoxy group such as methoxy;

iii) a $C_5$-$C_{12}$ aryl group which is optionally substituted by one or more hydroxyls and/or by one or more $C_1$-$C_4$ alkoxy radicals;

it being possible for $R_8$ and $R_9$ to form, with the nitrogen which carries them, a heterocycle having from 5 to 8 members, said heterocycle being able to contain one or more oxygen atoms and/or being optionally substituted by a $C_1$-$C_6$ hydrocarbon chain optionally containing one or more radicals selected from hydroxyl or $C_1$-$C_4$ alkoxy;

e) —$OR_4$ f) —$C(O)NHR_4$, where $R_4$ denotes a radical selected from —H, a $C_3$-$C_8$ branched or $C_1$-$C_8$ linear saturated alkyl group which is optionally substituted by one or more identical or different groups selected from:

i) —$COOR_6$, where $R_6$ is as defined above;

ii) a $C_5$-$C_{12}$ aryl radical, g) a radical of formula (III)

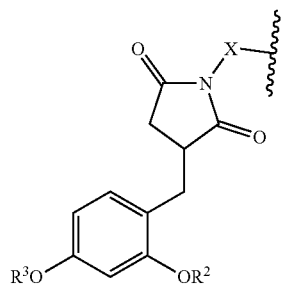

(III)

in which X denotes a $C_3$-$C_8$ cyclic or $C_3$-$C_6$ branched or $C_1$-$C_6$ linear saturated hydrocarbon chain or a $C_6$-$C_{12}$ arylene group such as phenylene, which is optionally substituted by one or more identical or different radicals selected from OH or a $C_1$-$C_6$ alkyl group, $R_2$ and $R_3$ have the same meanings as above; and when A denotes a radical of formula (III), all of the radicals $R_2$ and $R_3$ in the compounds of formula (II) are identical.

The compounds of formula (I) more preferably have the following meanings:

$R_2$ and $R_3$ independently denote a hydrogen atom or an acetyl group;

A denotes a radical selected from:

a) H b) a $C_3$-$C_8$ cyclic or $C_3$-$C_{16}$ branched or $C_2$-$C_{16}$ unsaturated or $C_1$-$C_{16}$ linear saturated alkyl group which is optionally interrupted by one or more heteroatoms selected from N and O and/or is optionally substituted by one or more identical or different groups selected from:

i) —OH ii) $C_1$-$C_4$ alkoxy, iii) —$CONH_2$;

iv) —$COOR_6$, where $R_6$ denotes H or a $C_3$-$C_4$ cyclic or $C_2$-$C_4$ unsaturated or $C_3$-$C_4$ branched or $C_1$-$C_4$ linear saturated alkyl group;

v) a phenyl group which is optionally substituted by one or more hydroxyls and/or by one or more $C_1$-$C_4$ alkoxy radicals;

vi) a saturated or unsaturated, non-aromatic heterocycle having from 5 to 8 members, comprising one or more nitrogen atoms, it being possible for one of the members to be a carbonyl moiety;

c) a $C_5$-$C_{12}$ aryl group such as phenyl;

d) —$NR_8R_9$, where $R_8$ and $R_9$, which are identical or different, denote H or a $C_3$-$C_8$ cyclic or $C_2$-$C_6$ unsaturated or $C_3$-$C_6$ branched or $C_1$-$C_6$ linear saturated alkyl group; or a $C_5$-$C_{12}$ aryl group such as phenyl;

it being possible for $R_8$ and $R_9$ to form, with the nitrogen which carries them, a heterocycle having from 5 to 8 members, it being possible for said heterocycle to contain an oxygen atom and/or being optionally substituted by a $C_1$-$C_6$ hydrocarbon chain optionally containing one or more radicals selected from hydroxyl or $C_1$-$C_4$ alkoxy;

e) —$OR_4$, where $R_4$ denotes H or a $C_3$-$C_6$ branched or $C_1$-$C_6$ linear saturated alkyl group which is optionally substituted by one or more identical or different groups selected from:

i) —COOH, ii) a $C_5$-$C_{12}$ aryl radical such as phenyl;

f) a radical of formula (III)

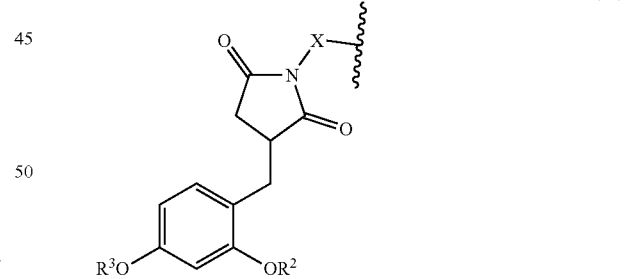

(III)

in which X denotes a $C_3$-$C_8$ cyclic or $C_3$-$C_6$ branched or $C_1$-$C_6$ linear saturated hydrocarbon chain or a $C_6$-$C_{12}$ arylene group such as phenylene, which is optionally substituted by one or more hydroxyl radicals;

$R_2$ and $R_3$ have the same meanings as above; and when A denotes a radical of formula (III), all of the radicals $R_2$ and $R_3$ in the compounds of formula (II) are identical.

Preferentially, $R_2$ and $R_3$=H for the compounds of formula (II).

A number of embodiments of compounds of formula (II) are described below:

$R_2$ and $R_3$=H, and A=H.

$R_2$ and $R_3$=H, and A=$C_3$-$C_{16}$ branched or $C_1$-$C_{16}$ saturated linear alkyl group.

$R_2$ and $R_3$=H, and A=$C_3$-$C_8$ branched or $C_1$-$C_8$ saturated linear alkyl group which is substituted by one or two hydroxyl groups and is optionally substituted by the group —$SR_5$, where $R_5$=H or $C_1$-$C_4$ alkyl.

$R_2$ and $R_3$=H, and A=phenyl or benzyl group.

$R_2$ and $R_3$=H, and A=$C_3$-$C_8$ branched or $C_1$-$C_8$ alkyl group which is substituted by a phenyl group which is optionally substituted by one or more hydroxyl groups and/or $C_1$-$C_4$ alkoxy group.

$R_2$ and $R_3$=H, and A=$C_3$-$C_8$ branched or $C_1$-$C_8$ saturated linear alkyl group which is substituted by a —COOH group, which is optionally substituted by the group $SR_5$, where $R_5$=H or $C_1$-$C_4$ alkyl.

$R_2$ and $R_3$=H, and A=$C_3$-$C_8$ branched or $C_1$-$C_8$ saturated linear alkyl group which is substituted by the group —$COOR_6$, where $R_6$ denotes a $C_1$-$C_6$ alkyl group, and is optionally substituted by a hydroxyl group and/or the group —$SR_5$, where $R_5$=H or $C_1$-$C_4$ alkyl and/or phenyl which is optionally substituted by one or more hydroxyls, or an imidazole radical.

$R_2$ and $R_3$=H, and A=$C_3$-$C_8$ branched or $C_1$-$C_8$ saturated linear alkyl group which is substituted by a —$CONH_2$ group, which is optionally substituted by a hydroxyl or phenyl group which is optionally substituted by one or more hydroxyls, or the group —$COOR_6$, where $R_6$ denotes a $C_1$-$C_6$ alkyl group.

$R_2$ and $R_3$=H, and A=group —$OR_4$, where $R_4$ denotes H, a $C_3$-$C_6$ branched or $C_1$-$C_6$ linear saturated alkyl group which is optionally substituted by a —COOH group or a phenyl group.

$R_2$ and $R_3$=H, and A=—$NR_8R_9$, where $R_8$ and $R_9$, which are identical or different, denote H or a $C_3$-$C_6$ branched or $C_1$-$C_6$ linear saturated alkyl group or a phenyl group; it being possible for $R_8$ and $R_9$ to form, with the nitrogen which carries them, a heterocycle which has 5 or 6 members and may contain an oxygen atom, said heterocycle being optionally substituted by a $C_1$-$C_6$ hydrocarbon chain optionally containing one or more radicals selected from hydroxyl or $C_1$-$C_4$ alkoxy.

$R_2$ and $R_3$=H, and A=$C_3$-$C_6$ branched or $C_2$-$C_6$ linear alkyl group interrupted by a —CONH— group and substituted by a COOH group.

$R_2$ and $R_3$=H, and A=$C_5$-$C_6$ cyclic alkyl group interrupted by a —CONH— group.

$R_2$ and $R_3$=H, and A=$C_5$-$C_6$ cyclic alkyl group interrupted by an oxygen atom.

$R_2$ and $R_3$=H, and A=radical of formula (II) as described above in which X denotes a $C_5$-$C_8$ cyclic or $C_3$-$C_6$ branched or $C_1$-$C_6$ linear saturated hydrocarbon chain or a phenylene group, which is optionally substituted by one or more hydroxyl groups.

Among these compounds, more particular preference is given to the following compounds:

| No. | Structure | Chemical Name |
|---|---|---|
| 1 | 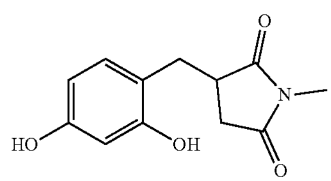 [SMILES: CN1C(=O)CC(Cc2ccc(O)cc2O)C1=O] | 3-(2,4-dihydroxybenzyl)-1-methylpyrrolidine-2,5-dione |
| 2 | 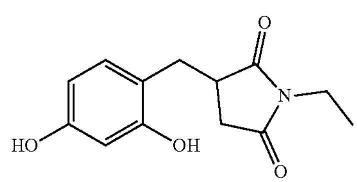 [SMILES: CCN1C(=O)CC(Cc2ccc(O)cc2O)C1=O] | 3-(2,4-dihydroxybenzyl)-1-ethylpyrrolidine-2,5-dione |
| 3 | 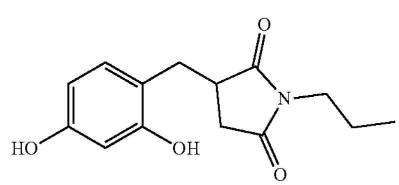 [SMILES: CCCN1C(=O)CC(Cc2ccc(O)cc2O)C1=O] | 3-(2,4-dihydroxybenzyl)-1-propylpyrrolidine-2,5-dione |
| 4 | 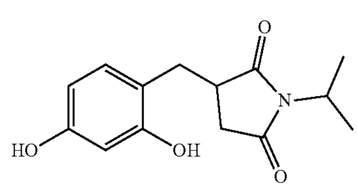 [SMILES: CC(C)N1C(=O)CC(Cc2ccc(O)cc2O)C1=O] | 3-(2,4-dihydroxybenzyl)-1-isopropylpyrrolidine-2,5-dione |

-continued

| No. | Structure | Chemical Name |
|---|---|---|
| 5 | 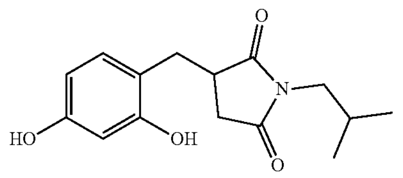 [SMILES: CC(C)CN1C(=O)CC(Cc2ccc(O)cc2O)C1=O] | 3-(2,4-dihydroxybenzyl)-1-isobutylpyrrolidine-2,5-dione |
| 6 | 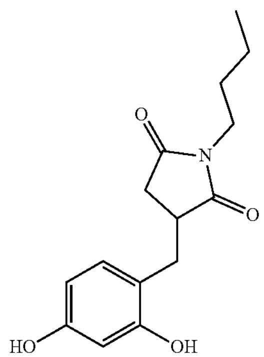 [SMILES: CCCCN1C(=O)CC(Cc2ccc(O)cc2O)C1=O] | 3-(2,4-dihydroxybenzyl)-1-butylpyrrolidine-2,5-dione |
| 7 | 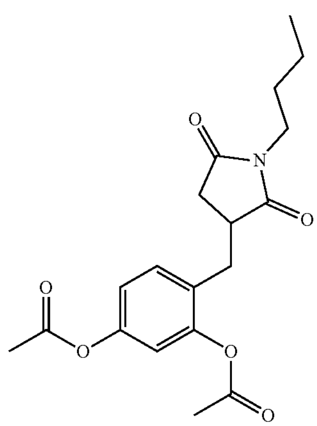 [SMILES: CCCCN1C(=O)CC(Cc2ccc(OC(C)=O)cc2OC(C)=O)C1=O] | 4-[(1-butyl-2,5-dioxopyrrolidin-3-yl)methyl]benzene-1,3-diyl diacetate |
| 8 | 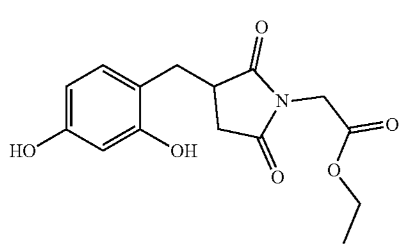 [SMILES: CCOC(=O)CN1C(=O)CC(Cc2ccc(O)cc2O)C1=O] | ethyl [3-(2,4-dihydroxybenzyl)-2,5-dioxopyrrolidin-1-yl]acetate |
| 9 | 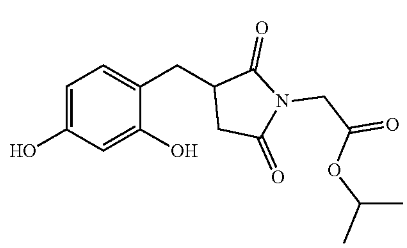 [SMILES: CC(C)OC(=O)CN1C(=O)CC(Cc2ccc(O)cc2O)C1=O] | isopropyl [3-(2,4-dihydroxybenzyl)-2,5-dioxopyrrolidin-1-yl]acetate |

-continued

| No. | Structure | Chemical Name |
|---|---|---|
| 10 | 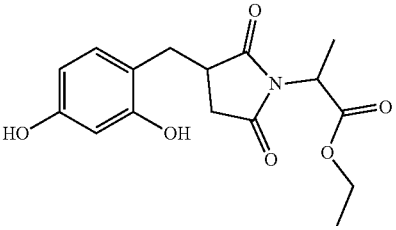 [SMILES: CCOC(=O)C(C)N1C(=O)CC(Cc2ccc(O)cc2O)C1=O] | ethyl 2-[3-(2,4-dihydroxybenzyl)-2,5-dioxopyrrolidin-1-yl]propanoate |
| 11 | 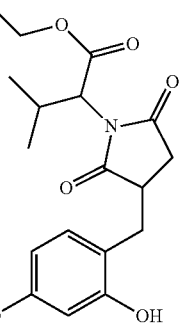 | ethyl 2-[3-(2,4-dihydroxybenzyl)-2,5-dioxopyrrolidin-1-yl]-3-methylbutanoate | and also their salts, their solvates, their optical isomers and their racemates.

The above compounds can be prepared in accordance with, for example, the process described in WO 2012/079938, the entirety of which is incorporated herein by reference.

In an embodiment, it may be preferable for the composition according to the present invention to include, as ingredient (a), resorcinol, butyl resorcinol, and/or phenylethyl resorcinol.

The amount of ingredient(s) (a) in the composition according to the present invention may be 0.01% by weight or more, preferably 0.1% by weight or more, and more preferably 1% by weight or more, relative to the total weight of the composition. It may be even more preferable that the amount of ingredient(s) (a) in the composition according to the present invention be 5% by weight or more, relative to the total weight of the composition.

On the other hand, the amount of ingredient(s) (a) in the composition according to the present invention may be 25% by weight or less, preferably 20% by weight or less, and more preferably 15% by weight or less, relative to the total weight of the composition. It may be even more preferable that the amount of ingredient(s) (a) in the composition according to the present invention be 12% by weight or less, relative to the total weight of the composition.

The amount of ingredient(s) (a) in the composition according to the present invention may range from 0.01 to 25% by weight, preferably from 0.1 to 20% by weight, and more preferably from 0.2 to 15% by weight, relative to the total weight of the composition.

[Lipophilic UV Filter]

The composition according to the present invention comprises (b) at least one lipophilic UV filter. A single type of lipophilic UV filter may be used, but two or more different types of lipophilic UV filter may be used in combination.

The term "lipophilic UV filter" means an organic molecule that is capable of screening out UV radiation between 290 and 400 nm, and which can be dissolved in a molecular form or dispersed in a fatty phase in order to obtain a macroscopically homogeneous phase. The term "organic molecule" means any molecule comprising in its structure one or more carbon atoms. Thus, the lipophilic UV filter used for the present invention may be active in the UV-A and/or UV-B region.

The lipophilic UV filter may be solid or liquid. The terms "solid" and "liquid" mean solid and liquid, respectively, at 25° C. under 1 atm.

The lipophilic UV filter may be chosen especially from cinnamic derivatives; anthranilates; salicylic derivatives; dibenzoylmethane derivatives, camphor derivatives; benzophenone derivatives; β,β-diphenylacrylate derivatives; triazine derivatives; benzotriazole derivatives; benzalmalonate derivatives, especially those mentioned in patent U.S. Pat. No. 5,624,663; imidazolines; p-aminobenzoic acid (PABA) derivatives; benzoxazole derivatives as described in patent applications EP 0 832 642, EP 1 027 883, EP 1 300 137, and DE 101 62 844; screening polymers and screening silicones such as those described especially in patent application WO 93/04665; α-alkylstyrene-based dimers, such as those described in patent application DE 198 55 649; 4,4-diarylbutadienes such as those described in patent applications EP 0 967 200, DE 197 46 654, DE 197 55 649, EP-A-1008 586, EP 1 133 980, and EP 133 981; merocyanin derivatives such as those described in patent applications WO 04/006 878, WO 05/058 269, WO 06/032 741, FR 2 957 249, and FR 2 957 250; and mixtures thereof.

As examples of the lipophilic UV filter, mention may be made of those denoted hereinbelow under their INCI names:

Dibenzoylmethane Derivative:

Butylmethoxydibenzoylmethane or avobenzone sold under the trade name Parsol 1789 by the company DSM Nutritional Products, Para-Aminobenzoic Acid Derivatives:

Ethyl PABA,

Ethyl Dihydroxypropyl PABA,

Ethylhexyl Dimethyl PABA sold in particular under the name Escalol 507 by ISP,

Salicylic Derivatives:

Homosalate sold under the name Eusolex HMS by Rona/EM Industries, Ethylhexyl salicylate sold under the name Neo Heliopan OS by Symrise, Cinnamic Derivatives:

Ethylhexyl methoxycinnamate sold especially under the trade name Parsol MCX by DSM Nutritional Products, Isopropyl methoxycinnamate, Isoamyl methoxycinnamate sold under the trade name Neo Heliopan E 1000 by Symrise, Cinoxate, Diisopropyl methylcinnamate, β,β-Diphenylacrylate derivatives:

Octocrylene sold especially under the trade name Uvinul N539 by BASF,

Etocrylene sold in particular under the trade name Uvinul N35 by BASF,

Benzophenone Derivatives:

Benzophenone-1 sold under the trade name Uvinul 400 by BASF,

Benzophenone-2 sold under the trade name Uvinul D50 by BASF,

Benzophenone-3 or oxybenzone sold under the trade name Uvinul M40 by BASF,

Benzophenone-6 sold under the trade name Helisorb 11 by Norquay,

Benzophenone-8 sold under the trade name Spectra-Sorb UV-24 by American Cyanamid, Benzophenone-12, N-hexyl 2-(4-diethylamino-2-hydroxybenzoyl)benzoate sold under the trade name Uvinul A+ or in the form of a mixture with octyl methoxycinnamate under the trade name Uvinul A+B by BASF, Benzylidenecamphor Derivatives:

3-Benzylidene Camphor manufactured under the name Mexoryl SD by Chimex,

4-Methylbenzylidene Camphor sold under the name Eusolex 6300 by Merck, Polyacrylamidomethylbenzylidenecamphor manufactured under the name Mexoryl SW by Chimex, Phenylbenzotriazole Derivatives:

Drometrizole trisiloxane sold under the name Silatrizole by Rhodia Chimie,

Triazine Derivatives:

Bis-(Ethylhexyloxyphenol) methoxyphenyl triazine sold under the trade name Tinosorb S by BASF, Ethylhexyl triazone sold in particular under the trade name Uvinul T150 by BASF, Diethylhexyl Butamido Triazone sold under the trade name Uvasorb HEB by Sigma 3V, 2,4,6-Tris(dineopentyl 4'-aminobenzalmalonate)-s-triazine, 2,4,6-Tris(diisobutyl 4'-aminobenzalmalonate)-s-triazine, 2,4-Bis(dineopentyl 4'-aminobenzalmalonate)-6-(n-butyl 4'-aminobenzoate)-s-triazine, the triazine silicones substituted by two aminobenzoate groups as those described in EP0841341 in particular 2,4-bis-(n-butyl 4'-aminobenzalmalonate)-6-[(3-{1,3,3,3-tetramethyl-1-[(trimethylsilyloxy] disiloxanyl}propyl)amino]-s-triazine, Anthranilic Derivatives:

Menthyl Anthranilate sold under the trade name Neo Heliopan MA by Symrise,

Imidazoline Derivatives:

Ethylhexyl dimethoxybenzylidene dioxoimidaoline propionate,

Benzalmalonate Derivatives:

Dineopentyl 4'-methoxybenzalmalonate,

Polyorganosiloxane containing benzalmalonate functions, for instance Polysilicone-15, sold under the trade name Parsol SLX by DSM, 4,4-Diarylbutadiene Derivatives:

1,1-dicarboxy(2,2'-dimethylpropyl)-4,4-diphenylbutadiene,

Lipophilic merocyanin derivatives:

Octyl 5-N,N-diethylamino-2-phenylsulfonyl-2,4-pentadienoate and mixtures thereof.

Preferable lipophilic UV filters may be chosen from:

Butylmethoxydibenzoylmethane,

Ethylhexyl methoxycinnamate,

Ethylhexyl salicylate,

Homosalate,

Butylmethoxydibenzoylmethane,

Octocrylene,

Benzophenone-3, n-Hexyl 2-(4-diethylamino-2-hydroxybenzoyl)benzoate,

4-Methylbenzylidenecamphor,

Bis(ethylhexyloxyphenol)methoxyphenyltriazine,

Ethylhexyl triazone,

Diethylhexyl Butamido Triazone, 2,4-bis-(n-butyl 4'-aminobenzalmalonate)-6-[(3-{1,3,3,3-tetramethyl-1-[(trimethylsilyloxy]-disiloxanyl}propyl)amino]-s-triazine, Drometrizole Trisiloxane, Polysilicone-15, 1,1-dicarboxy(2,2'-dimethylpropyl)-4,4-diphenylbutadiene, and mixtures thereof.

More preferable lipophilic UV filters may be chosen from:

Butylmethoxydibenzoylmethane,

Ethylhexyl methoxycinnamate,

Octocrylene,

Ethylhexyl salicylate, n-Hexyl 2-(4-diethylamino-2-hydroxybenzoyl)benzoate,

Bis(ethylhexyloxyphenol)methoxyphenyltriazine, 2,4-bis-(n-butyl 4'-aminobenzalmalonate)-6-[(3-{1,3,3,3-tetramethyl-1-[(trimethylsilyloxy]-disiloxanyl}propyl)amino]-s-triazine, Ethylhexyl triazone, Diethylhexyl Butamido Triazone, Drometrizole trisiloxane, and mixtures thereof.

In an embodiment, it may be preferable for the composition according to the present invention to include, as ingredient (b), bis(ethylhexyloxyphenol)methoxyphenyltriazine resorcinol and/or drometrizole trisiloxane.

The amount of ingredient(s) (b) in the composition according to the present invention may be 0.01% by weight or more, preferably 0.1% by weight or more, and more preferably 1% by weight or more, relative to the total weight of the composition. It may be even more preferable that the amount of ingredient(s) (b) in the composition according to the present invention be 3% by weight or more, relative to the total weight of the composition.

On the other hand, the amount of ingredient(s) (b) in the composition according to the present invention may be 25% by weight or less, preferably 20% by weight or less, and more preferably 15% by weight or less, relative to the total weight of the composition. It may be even more preferable that the amount of ingredient(s) (b) in the composition according to the present invention be 12% by weight or less, relative to the total weight of the composition.

The amount of ingredient(s) (b) in the composition according to the present invention may range from 0.01 to 25% by weight, preferably from 0.1 to 20% by weight, and more preferably from 1 to 15% by weight, relative to the total weight of the composition. It may be even more preferable that the amount of ingredient(s) (b) in the composition according to the present invention be from 3% to 12% by weight, relative to the total weight of the composition.

[Lipophilic Antioxidant Agent]

The composition according to the present invention comprises (c) at least one lipophilic antioxidant agent. A single type of lipophilic antioxidant agent may be used, but two or more different types of lipophilic antioxidant agent may be used in combination.

According to the present invention, antioxidant agents are compounds or substances that can scavenge the various radical forms which may be present in the skin; preferably, they simultaneously scavenge all the various radical forms present.

As antioxidant agents, mention may be made of, phenolic antioxidants which have a hindered phenol structure or a semi-hindered phenol structure within the molecule. As specific examples of such compounds, mention may be made of, 3,5-bis(1,1-dimethylethyl)-4-hydroxybenzenepropanoic acid) which has INCI name of pentaerythrityl tetra-di-t-butyl hydroxyhydrocinnamate, 2,6-di-tert-butyl-4-methylphenol, 2,6-di-tert-butyl-4-ethylphenol, mono- or di- or tri-(α-methylbenzyl)phenol, 2,2'-methylenebis(4-ethyl-6-tert-butylphenol), 2,2'-methylenebis(4-methyl-6-tert-butylphenol), 4,4'-butylidenebis(3-methyl-6-tert-butylphenol), 4,4'-thiobis(3-methyl-6-tert-butylphenol), 2,5-di-tert-butylhydroquinone, 2,5-di-tert-amylhydroquinone, tris[N-(3,5-di-tert-butyl-4-hydroxybenzyl)]isocyanurate, 1,1,3-tris(2-methyl-4-hydroxy-5-tert-butylphenyl)butane, butylidene-1,1bis[3-(3-tert-butyl-4-hydroxy-5-methylphenyl)propionate], octadecyl 3-(3,5-di-tert-butyl-4-hydroxyphenyl)propionate, tetrakis[methylene-3-(3,5-di-tert-butyl-4-hydroxyphenyl) propionato]methane, triethylene glycol bis[3-(3-tert-butyl-4-hydroxy-5-methylphenyl)propionate], 3,9-bis {2-[3-(3-tert-butyl-4-hydroxy-5-methylphenyl)propionyloxy]-1,1-dimethylethyl}-2,4,8,10-tetraoxaspiro [5.5]undecane, 1,3,5-trimethyl-2,4,6-tris(3,5-di-tert-butyl-4-hydroxybenzyl)benzene, 2,2-thiodiethylenebis[3-(3,5-di-tert-butyl-4-hydroxyphenyl) propionate], N,N'-hexamethylenebis(3,5-di-tert-butyl-4-hydroxyhydrocinnamide), 1,6-hexanediol bis[3-(3,5-di-tert-butyl-4-hydroxyphenyl)propionate], 1,3,5-tris[(4-tert-butyl-3-hydroxy-2,6-xylyl)methyl]-1,3,5-triazine-2,4,6-trione, 2,4-bis(n-octylthio)-6-(4-hydroxy-3,5-di-tert-butylanilino)-1,3,5-triazine, 2-tert-butyl-6-(3'-tert-butyl-5'-methyl-2'-hydroxybenzyl)-4-methylphenyl acrylate, 2-[1-(2-hydroxy-3,5-di-tert-pentylphenyl)ethyl]-4,6-di-tert-pentylphenyl acrylate, 4,6-bis[(octylthio)methyl]-o-cresol, 2,4-di-tert-butylphenyl-3,5-di-tert-butyl-4-hydroxybenzoate and 1,6-hexanediolbis[3-(3,5-di-tert-butyl-4-hydroxyphenyl) propionate].

As antioxidant agents, mention may be made of: BHA (butylated hydroxyl anisole) and BHT (butylated hydroxyl toluene), vitamin E (or tocopherols and tocotrienol) and derivatives thereof, such as the phosphate derivative, for instance TPNA® sold by the company Showa Denko, coenzyme Q10 (or ubiquinone), idebenone, certain carotenoids such as lutein, astaxanthin, beta-carotene, polyphenols, phenolic acids and derivatives (e.g., chlorogenic acid), and flavonoids, which represent the main subgroup of polyphenols.

Among the flavonoids, mention may be made especially of chalcones, hydroxylated chalcones and reduced derivatives thereof (as described especially in patent FR 2 608 150), for instance phloretin, neohesperidin, phloridzin, aspalathin, etc., flavanones, for instance hesperetin and naringin, flavonols, for instance quercetin, rutin, flavanols, for instance catechin, EGCG, flavones, for instance apigenidin, and finally anthocyans. Mention may also be made of tannins. Reference may also be made to the compounds described in patent applications FR 2 699 818, FR 2 706 478, FR 2 907 339, FR 2 81.4 943 and FR 2 873 026.

Polyphenol compounds may especially be derived from plant extracts chosen from extracts of green tea, apple, hop, guava, cocoa or wood, such as chestnut, oak, horse chestnut or hazel. It is also possible to use an extract of *pinaster* bark, for example obtained according to processes described in U.S. Pat. Nos. 4,698,360, 6,372,266 and 5,720,956. As examples of such extracts, the compound referenced as INCI name *pinus pinaster* (bark extract) and as CTFA name Pine (*pinus pinaster*) bark extract may be cited. It may in particular be the extract of *pinaster* bark marketed under the PYCNOGENOL® reference by the BIOLANDES AROMES firm and/or HORPHAG Research. The extracts (Maritime) pine bark from LAYN Natural Ingredients, Pine Bark from Blue Calif., and also Oligopin® from D.R.T. (Les Derives Resiniques et Terpeniques) may also be cited.

In the context of the present invention, the term "polyphenol compound" thus also covers the plant extract itself, rich in these polyphenol compounds.

Antioxidants that may also be mentioned include dithiolanes, for instance asparagusic acid, or derivatives thereof, for instance siliceous dithiolane derivatives, especially such as those described in patent application FR 2 908 769.

Antioxidants that may also be mentioned include:

glutathione and derivatives thereof (GSH and/or GSHOEt), such as glutathione alkyl esters (such as those described in patent applications FR 2 704 754 and FR 2 908 769);

cysteine and derivatives thereof, such as N-acetylcysteine or L-2-oxothiazolidine-4-carboxylic acid. Reference may also be made to the cysteine derivatives described in patent applications FR 2 877 004 and FR 2 854 160;

ferulic acid and derivatives thereof (esters, salts, etc.). Mention may particularly be made of esters of ferulic acid and of C1-C30 alcohols, in particular methyl ferulate, ethyl ferulate, isopropyl ferulate, octyl ferulate and oryzanyl ferulate;

certain enzymes for defending against oxidative stress, such as catalase, superoxide dismutase (SOD), lactoperoxidase, glutathione peroxidase and quinone reductases;

benzylcyclanones; substituted naphthalenones; pidolates (as described especially in patent application EP 0 511 118);

caffeic acid and derivatives thereof, gamma-oryzanol; melatonin, sulforaphane and extracts containing it (excluding cress);

the diisopropyl ester of N,N'-bis(benzyl)ethylenediamine-N,N'-diacetic acid, as described especially in patent applications WO 94/11338, FR 2 698 095, FR 2 737 205 or EP 0 755 925; deferoxamine (or desferal) as described in patent application FR 2 825 920.

The antioxidants that are preferably used are the chalcones, more particularly phloretin or neohesperidin, the diisopropyl ester of N,N'-bis(benzyl)ethylenediamine-N,N'-diacetic acid or an extract of *pinaster* bark such as PYCNOGENOL®.

The (c) lipophilic antioxidant agent means that the partition coefficient of the antioxidant agent between n-butanol and water is >1, more preferably >10 and even more preferably >100.

As examples of the (c) lipophilic antioxidant agent, mention may be made of pentaerythrityl tetra-di-t-butyl hydroxyhydrocinnamate, nordihydroguaiaretic acid, ferulic acid, resveratrol, propyl gallate, butylated hydroxyl toluene, butylated hydroxyl anisole, ascorbyl palmitate, tocopherol, and mixtures thereof.

The amount of ingredient(s) (c) in the composition according to the present invention may be 0.01% by weight or more, preferably 0.05% by weight or more, and more preferably 0.1% by weight or more, relative to the total weight of the composition. It may be even more preferable that the amount of ingredient(s) (c) in the composition according to the present invention be 0.3% by weight or more, relative to the total weight of the composition.

On the other hand, the amount of ingredient(s) (c) in the composition according to the present invention may be 20% by weight or less, preferably 15% by weight or less, and more preferably 10% by weight or less, relative to the total weight of the composition. It may be even more preferable that the amount of ingredient(s) (c) in the composition according to the present invention be 5% by weight or less, relative to the total weight of the composition.

The amount of ingredient(s) (c) in the composition according to the present invention may range from 0.01 to 20% by weight, preferably from 0.05 to 15% by weight, and more preferably from 0.1 to 10% by weight, relative to the total weight of the composition. It may be even more preferable that the amount of ingredient(s) (c) in the composition according to the present invention be from 0.3% to 5% by weight, relative to the total weight of the composition.

[Oil]

The composition according to the present invention comprises (d) at least one oil. A single type of oil may be used, but two or more different types of oils may be used in combination.

Here, "oil" means a fatty compound or substance which is in the form of a liquid or a paste (non-solid) at room temperature (25° C.) under atmospheric pressure (760 mmHg). As the oil(s), those generally used in cosmetics can be used alone or in combination thereof. These oil(s) may be volatile or non-volatile, preferably non-volatile.

The (d) oil may be a non-polar oil such as a hydrocarbon oil, a silicone oil, or the like; a polar oil such as a plant or animal oil and an ester oil or an ether oil; or a mixture thereof.

The (d) oil may be selected from the group consisting of oils of plant or animal origin, synthetic oils, silicone oils, hydrocarbon oils and fatty alcohols.

As examples of plant oils, mention may be made of, for example, linseed oil, *camellia* oil, macadamia nut oil, corn oil, mink oil, olive oil, avocado oil, sasanqua oil, castor oil, safflower oil, jojoba oil, sunflower oil, almond oil, rapeseed oil, sesame oil, soybean oil, peanut oil, and mixtures thereof.

As examples of synthetic oils, mention may be made of alkane oils such as isododecane and isohexadecane, ester oils, ether oils, and artificial triglycerides.

The ester oils are preferably liquid esters of saturated or unsaturated, linear or branched $C_1$-$C_{26}$ aliphatic monoacids or polyacids and of saturated or unsaturated, linear or branched $C_1$-$C_{26}$ aliphatic monoalcohols or polyalcohols, the total number of carbon atoms of the esters being greater than or equal to 10.

Preferably, for the esters of monoalcohols, at least one from among the alcohol and the acid from which the esters of the present invention are derived is branched.

Among the monoesters of monoacids and of monoalcohols, mention may be made of ethyl palmitate, ethyl hexyl palmitate, isopropyl palmitate, dicaprylyl carbonate, alkyl myristates such as isopropyl myristate or ethyl myristate, isocetyl stearate, 2-ethylhexyl isononanoate, isononyl isononanoate, isodecyl neopentanoate and isostearyl neopentanoate.

Esters of $C_4$-$C_{22}$ dicarboxylic or tricarboxylic acids and of $C_1$-$C_{22}$ alcohols, and esters of monocarboxylic, dicarboxylic or tricarboxylic acids and of non-sugar $C_4$-$C_{26}$ dihydroxy, trihydroxy, tetrahydroxy or pentahydroxy alcohols may also be used.

Mention may especially be made of: diethyl sebacate; isopropyl lauroyl sarcosinate; diisopropyl sebacate; bis(2-ethylhexyl) sebacate; diisopropyl adipate; di-n-propyl adipate; dioctyl adipate; bis(2-ethylhexyl) adipate; diisostearyl adipate; bis(2-ethylhexyl) maleate; triisopropyl citrate; triisocetyl citrate; triisostearyl citrate; glyceryl trilactate; glyceryl trioctanoate; trioctyldodecyl citrate; trioleyl citrate; neopentyl glycol diheptanoate; diethylene glycol diisononanoate.

As ester oils, one can use sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars may be monosaccharides, oligosaccharides or polysaccharides.

Examples of suitable sugars that may be mentioned include sucrose (or saccharose), glucose, galactose, ribose, fucose, maltose, fructose, mannose, arabinose, xylose and lactose, and derivatives thereof, especially alkyl derivatives, such as methyl derivatives, for instance methylglucose.

The sugar esters of fatty acids may be chosen especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may have one to three conjugated or non-conjugated carbon-carbon double bonds.

The esters according to this variant may also be selected from monoesters, diesters, triesters, tetraesters and polyesters, and mixtures thereof.

These esters may be, for example, oleates, laurates, palmitates, myristates, behenates, cocoates, stearates, linoleates, linolenates, caprates and arachidonates, or mixtures thereof such as, especially, oleopalmitate, oleostearate and palmitostearate mixed esters, as well as pentaerythrityl tetraethyl hexanoate.

More particularly, use is made of monoesters and diesters and especially sucrose, glucose or methylglucose monooleates or dioleates, stearates, behenates, oleopalmitates, linoleates, linolenates and oleostearates.

An example that may be mentioned is the product sold under the name Glucate® DO by the company Amerchol, which is a methylglucose dioleate.

As examples of preferable ester oils, mention may be made of; for example, diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

As examples of artificial triglycerides, mention may be made of; for example, capryl caprylyl glycerides, glyceryl trimyristate, glyceryl tripalmitate, glyceryl trilinolenate, glyceryl trilaurate, glyceryl tricaprate, glyceryl tricaprylate, glyceryl tri(caprate/caprylate) and glyceryl tri(caprate/caprylate/linolenate).

As examples of silicone oils, mention may be made of, for example, linear organopolysiloxanes such as dimethylpolysiloxane, methylphenylpolysiloxane, methylhydrogenpolysiloxane, and the like; cyclic organopolysiloxanes such as cyclohexasiloxane, octamethylcyclotetrasiloxane, decamethylcyclopentasiloxane, dodecamethylcyclohexasiloxane, and the like; and mixtures thereof.

Preferably, silicone oil is chosen from liquid polydialkylsiloxanes, especially liquid polydimethylsiloxanes (PDMS) and liquid polyorganosiloxanes comprising at least one aryl group.

These silicone oils may also be organomodified. The organomodified silicones that can be used in accordance with the present invention are silicone oils as defined above and comprise in their structure one or more organofunctional groups attached via a hydrocarbon-based group.

Organopolysiloxanes are defined in greater detail in Walter Noll's Chemistry and Technology of Silicones (1968), Academic Press. They may be volatile or non-volatile.

When they are volatile, the silicones are more particularly chosen from those having a boiling point of between 60° C. and 260° C., and even more particularly from:

(i) cyclic polydialkylsiloxanes comprising from 3 to 7 and preferably 4 to 5 silicon atoms.

These are, for example, octamethylcyclotetrasiloxane sold in particular under the name Volatile Silicone® 7207 by Union Carbide or Silbione® 70045 V2 by Rhodia, decamethylcyclopentasiloxane sold under the name Volatile Silicone® 7158 by Union Carbide, Silbione® 70045 V5 by Rhodia, and dodecamethylcyclopentasiloxane sold under the name Silsoft 1217 by Momentive Performance Materials, and mixtures thereof. Mention may also be made of cyclocopolymers of the type such as dimethylsiloxane/methylalkylsiloxane, such as Silicone Volatile® FZ 3109 sold by the company Union Carbide, of formula:

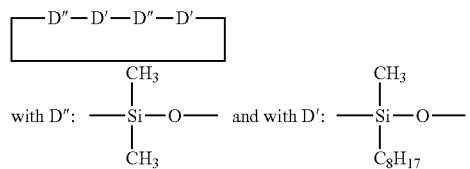

Mention may also be made of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2', 2',3,3'-hexatrimethylsilyloxy)neopentane;

(ii) linear volatile polydialkylsiloxanes containing 2 to 9 silicon atoms and having a viscosity of less than or equal to $5 \times 10^{-6}$ m$^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*. The viscosity of the silicones is measured at 25° C. according to ASTM standard 445 Appendix C.

Non-volatile polydialkylsiloxanes may also be used. These non-volatile silicones are more particularly chosen from polydialkylsiloxanes, among which mention may be made mainly of polydimethylsiloxanes containing trimethylsilyl end groups.

Among these polydialkylsiloxanes, mention may be made, in a non-limiting manner, of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm$^2$/s;

the Viscasil® oils from General Electric and certain oils of the SF series (SF 96, SF 18) from General Electric.

Mention may also be made of polydimethylsiloxanes containing dimethylsilanol end groups known under the name dimethiconol (CTFA), such as the oils of the 48 series from the company Rhodia.

Among the silicones containing aryl groups are polydiarylsiloxanes, especially polydiphenylsiloxanes and polyalkylarylsiloxanes. Examples that may be mentioned include the products sold under the following names:

the Silbione® oils of the 70 641 series from Rhodia;

the oils of the Rhodorsil® 70 633 and 763 series from Rhodia;

the oil Dow Corning 556 Cosmetic Grade Fluid from Dow Corning;

the silicones of the PK series from Bayer, such as the product PK20;

certain oils of the SF series from General Electric, such as SF 1023, SF 1154, SF 1250 and SF 1265.

The organomodified liquid silicones may especially contain polyethyleneoxy and/or polypropyleneoxy groups. Mention may thus be made of the silicone KF-6017 proposed by Shin-Etsu, and the oils Silwet® L722 and L77 from the company Union Carbide.

Hydrocarbon oils may be chosen from:

linear or branched, optionally cyclic, C$_6$-C$_{16}$ lower alkanes. Examples that may be mentioned include hexane, undecane, dodecane, tridecane, and isoparaffins, for instance isohexadecane, isododecane and isodecane; and linear or branched hydrocarbons containing more than 16 carbon atoms, such as liquid paraffins, liquid petroleum jelly, polydecenes and hydrogenated polyisobutenes such as Parleam®, and squalane.

As preferable examples of hydrocarbon oils, mention may be made of, for example, linear or branched hydrocarbons such as isohexadecane, isododecane, squalane, mineral oil (e.g., liquid paraffin), paraffin, vaseline or petrolatum, naphthalenes, and the like; hydrogenated polyisobutene, isoeicosan, and decene/butene copolymer; and mixtures thereof.

The term "fatty" in the fatty alcohol means the inclusion of a relatively large number of carbon atoms. Thus, alcohols which have 4 or more, preferably 6 or more, and more preferably 12 or more carbon atoms are encompassed within the scope of fatty alcohols. The fatty alcohol may be saturated or unsaturated. The fatty alcohol may be linear or branched.

The fatty alcohol may have the structure R—OH wherein R is chosen from saturated and unsaturated, linear and branched radicals containing from 4 to 40 carbon atoms, preferably from 6 to 30 carbon atoms, and more preferably from 12 to 20 carbon atoms. In at least one embodiment, R may be chosen from $C_{12}$-$C_{20}$ alkyl and $C_{12}$-$C_{20}$ alkenyl groups. R may be or may not be substituted with at least one hydroxyl group.

As examples of the fatty alcohol, mention may be made of lauryl alcohol, cetyl alcohol, stearyl alcohol, isostearyl alcohol, behenyl alcohol, undecylenyl alcohol, myristyl alcohol, octyldodecanol, hexyldecanol, oleyl alcohol, linoleyl alcohol, palmitoleyl alcohol, arachidonyl alcohol, erucyl alcohol, and mixtures thereof.

It is preferable that fatty alcohol be a saturated fatty alcohol.

Thus, the fatty alcohol may be selected from straight or branched, saturated or unsaturated $C_6$-$C_{30}$ alcohols, preferably straight or branched, saturated $C_6$-$C_{30}$ alcohols, and more preferably straight or branched, saturated $C_{12}$-$C_{20}$ alcohols.

The term "saturated fatty alcohol" here means an alcohol having a long aliphatic saturated carbon chain. It is preferable that the saturated fatty alcohol be selected from any linear or branched, saturated $C_6$-$C_{30}$ fatty alcohols. Among the linear or branched, saturated $C_6$-$C_{30}$ fatty alcohols, linear or branched, saturated $C_{12}$-$C_{20}$ fatty alcohols may preferably be used. Any linear or branched, saturated $C_{16}$-$C_{20}$ fatty alcohols may be more preferably used. Branched $C_{16}$-$C_{20}$ fatty alcohols may be even more preferably used.

As examples of saturated fatty alcohols, mention may be made of isostearyl alcohol, octyldodecanol, hexyldecanol, and mixtures thereof. In one embodiment, octyldodecanol, hexyldecanol, or a mixture thereof; can be used as a saturated fatty alcohol.

According to at least one embodiment, the fatty alcohol used in the composition according to the present invention is preferably chosen from octyldodecanol, hexyldecanol and mixtures thereof.

It is preferable that the (d) oil be chosen from polar oils, more preferably ester oils. In other words, it is preferable that the (d) oil comprise at least one polar oil, and more preferably at least one ester oil.

It may be preferable that the (d) oil be chosen from oils with a molecular weight below 600 g/mol.

The amount of ingredient(s) (d) in the composition according to the present invention may be 50% by weight or more, preferably 60% by weight or more, and more preferably 70% by weight or more, relative to the total weight of the composition. It may be even more preferable that the amount of ingredient(s) (d) in the composition according to the present invention be 75% by weight or more, relative to the total weight of the composition.

On the other hand, the amount of ingredient(s) (d) in the composition according to the present invention may be 95% by weight or less, preferably 93% by weight or less, and more preferably 90% by weight or less, relative to the total weight of the composition. It may be even more preferable that the amount of ingredient(s) (d) in the composition according to the present invention be 87% by weight or less, relative to the total weight of the composition.

The amount of ingredient(s) (d) in the composition according to the present invention may range from 50 to 95% by weight, preferably from 60 to 93% by weight, more preferably from 70 to 90% by weight, relative to the total weight of the composition. It may be even more preferable that the amount of ingredient(s) (d) in the composition according to the present invention be from 75% to 87% by weight, relative to the total weight of the composition.

[Water]

It is preferable that the composition according to the present invention be anhydrous.

The term "anhydrous" here means that the composition according to the present invention may contain only a small amount of water, preferably no water. Thus, the amount of water may be 2% by weight or less, preferably 1.5% by weight or less, and more preferably 1% by weight or less relative to the total weight of the composition. It is particularly preferable that the cosmetic composition according to the present invention contains no water.

[Lipophilic Thickener]

The compositions of the present invention may contain a lipophilic thickener. Lipophilic thickeners may be chosen from gelling agents derived from glutamic acid, gelling agents in polymeric form, and gelling agents in mineral form. The gelling agent includes agents that gel via chemical reticulation and agents that gel via physical reticulation.

N-acyl glutamic acid derivative may be used as gelling agents derived from glutamic acid. N-acyl glutamic acid derivatives include N-acyl glutamic acid amides and N-acyl glutamic acid esters. In one embodiment, N-acyl glutamic acid amides in which the acyl group represents a $C_8$ to $C_{22}$ alkyl chain are preferred.

Examples of N-acyl glutamic acid derivatives that may be mentioned include N-lauroyl-glutamic acid diethyl amide, N-lauroyl-glutamic acid dibutyl amide, N-lauroyl-glutamic acid dihexyl amide, N-lauroyl-glutamic acid dioctyl amide, N-lauroyl-glutamic acid didecyl amide, N-lauroyl-glutamic acid didodecyl amide, N-lauroyl-glutamic acid ditetradecyl amide, N-lauroyl-glutamic acid dihexadecyl amide, N-lauroyl-glutamic acid distearyl amide, N-ethylhexanoyl -L-glutamic acid dibutyl amide, N-stearoyl-glutamic acid dibutyl amide, N-stearoyl-glutamic acid dihexyl amide, N-stearoyl-glutamic acid diheptyl amide, N-stearoyl-glutamic acid dioctyl amide, N-stearoyl-glutamic acid didecyl amide, N-stearoyl-glutamic acid didodecyl amide, N-stearoyl-glutamic acid ditetradecyl amide, N-stearoyl-glutamic acid dihexadecyl amide, N-stearoyl-glutamic acid distearyl amide and mixtures thereof, more preferred, is N-lauroyl-glutamic acid dibutyl amide, N-stearyl-glutamic acid dihexyl amide, and mixtures thereof.

The gelling agent is preferably N-acyl glutamic acid dialkylamide, and more preferably N-lauroyl-L-glutamic acid dibutylamide (INCI: dibutyl lauroyl glutamide), manufactured or sold by Ajinomoto under the name GP-1 and N-ethylhexanoyl -L-glutamic acid dibutylamide (INCI: dibutyl ethylhexanoyl glutamide), manufactured or sold by Ajinomoto under the name EB-21.

Lipophilic polyamide polymers may be used as gelling agents in polymeric form. As lipophilic polyamide polymers, mention may be made of polyamides branched with pendant fatty chains and/or terminal fatty chains containing from 12 to 120 carbon atoms and in particular from 12 to 68 carbon atoms, the terminal fatty chains being bonded to the polyamide backbone via ester groups. These polymers are more especially those described in document U.S. Pat. No. 5,783,657 from the company Union Camp. In particular, mention may be made of the polymers of which the INCI name is "ethylenediamine/stearyl dimer dilinoleate copolymer" and "ethylenediamine/stearyl dimer tallate copolymer".

By way of examples of gelling agents, mention may be made of the commercial products sold by the company Bush Boake Allen under the names Uniclear 80, Uniclear 100, Uniclear 80 V, Uniclear 100 V and Uniclear 100 VG They are sold, respectively, in the form of a gel at 80% (with respect to active material) in a mineral oil and at 100% (with respect to active material).

Modified clays may be used as gelling agents, examples of which include hectorites modified with an ammonium chloride of a $C_{10}$ to $C_{22}$ fatty acid, such as bentonite modified with distearyldimethylammonium chloride, also known as quaternium-18 bentonite, such as the products sold or made under the names Bentone 34 and Bentone 38 VCG by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox.

A lipophilic thickener, if present, is in amounts generally ranging from about 0.01% to about 30% relative to the total weight of the composition. In certain embodiments, the lipophilic thickener is present in an amount of from about 0.1% to about 25%, by weight, in other embodiments from about 0.5% to about 23%, by weightbased on the total weight of the composition.

[Other Aspects]

It may be preferable that the weight ratio of (the amount of ingredients (a), (b) and (c))/(the amount of ingredient (d)) in the composition according to the present invention be 0.5 or less, preferably 0.4 or less, and more preferably 0.35 or less.

If the above weight ratio is 0.5 or less, the temperature-stability may be improved or enhanced, and therefore, precipitations in the composition according to the present invention may be reduced or avoided.

The present invention may relate to the use of ingredients (b) and (c) in a composition including ingredients (a) and (d) to improve or enhance the photostability and/or temperature-stability of the composition.

[Other Ingredients]

The composition according to the present invention is advantageously a cosmetic composition.

The composition according to the present invention may also comprise an effective amount of other ingredients, known previously elsewhere in cosmetic compositions, such as various common adjuvants, anti-ageing agents, whitening agents other than ingredient (a), anti-greasy skin agents, sequestering agents such as EDTA and etidronic acid, UV screening agents other than ingredient (b), silicones, preserving agents, vitamins or provitamins, for instance, panthenol, ° pacifiers, fragrances, plant extracts, thickeners, cationic polymers and so on.

[Preparation]

The composition according to the present invention can be prepared by mixing ingredients (a) to (d), as essential ingredients, as well as optional ingredient(s), as explained above.

The method and means to mix the above essential and optional ingredients are not limited. Any conventional method and means can be used to mix the above essential and optional ingredients to prepare the composition according to the present invention.

The composition according to the present invention can be uniform.

The composition according to the present invention can be in the form of a transparent or translucent liquid, gel or solid. In particular, the composition according to the present invention can be in the form of a transparent liquid, gel or solid, because the change in color of the composition due to exposure to light and/or under relatively high temperatures can be reduced or avoided.

The transparency may be measured by measuring the transmittance with an absorption spectrometer in the visible region (for example, transparency was measured with a V-550 (JASCO) with a 2 mm width cell as an average of visible light transmittance (between 400 and 800 nm)). The measurement is taken on the undiluted composition. The blank is determined with distilled water.

The composition of the present invention may preferably have a transparency greater than 50%, preferably greater than 60%, more preferably greater than 70%, even more preferably greater than 80%, and most preferably greater than 90%.

[Process]

The composition according to the present invention can be used in a cosmetic process for a keratin substance comprising the step of applying the composition according to the present invention to the keratin substance. The keratin substance here means a material containing keratin as a main constituent element, and examples thereof include skin, mucous membranes, lips, nails and the like.

Since the composition according to the present invention includes (a) compound selected from the group consisting of resorcinol and resorcinol derivatives, it is preferable that the composition according to the present invention be used for whitening a keratin substance. For example, the composition according to the present invention may be used as a whitening product.

The present invention may also relate to a use of the composition according to the present invention, as it is or in care products and/or make-up products for body and/or facial skin and/or mucous membranes and/or lips and/or nails.

In other words, the composition according to the present invention can be used, as it is, as the above product. Alternatively, the composition according to the present invention can be used as an element of the above product. For example the composition according to the present invention can be added to or combined with any other elements to form the above product.

The care product may be in the form of not only a liquid but also a stick, a bar, and the like. The make-up product may be a foundation, a mascara, a lipstick, a lip gloss, a blusher, a nail varnish, and the like.

EXAMPLES

The present invention will be described in more detail by way of examples, which however should not be construed as limiting the scope of the present invention.

Examples 1-5 and Comparative Examples 1-3

The following compositions according to Examples 1-5 and Comparative Examples 1-3, shown in Table 1, were prepared by mixing the components shown in Table 1. The numerical values for the amounts of the components shown in Table 1 are all based on "% by weight" as active raw materials.

Very Good: Almost the same condition as production. No color change and no crystallization were observed.

Good: Change in color and odor could be somewhat observed. No crystallization, transparent aspect was observed and kept.

Poor: Change in color, odor, and presence of crystallization could be clearly observed.

TABLE 1

|     |                                                          |                  | Ex. 1 | Ex. 2 | Ex. 3 | Ex. 4 | Ex. 5 | Comp. Ex. 1 | Comp. Ex. 2 | Comp. Ex. 3 |
|-----|----------------------------------------------------------|------------------|-------|-------|-------|-------|-------|-------------|-------------|-------------|
| (a) | Phenylethyl resorcinol                                   |                  | 10    | 10    | 10    | 10    | 10    | 10          | 10          | 10          |
| (b) | Drometrizole Trisiloxane                                 |                  | 10    | 3.5   | 3.5   | —     | 3.5   | —           | 3.5         | —           |
|     | Bis-Ethylhexyloxyphenol methoxyphenyl triazine           |                  | —     | —     | —     | 3.5   | —     | —           | —           | —           |
| (c) | Pentaerythrityl tetra-di-t-butyl hydroxyhydrocinnamate   |                  | 3.5   | 3.5   | 0.5   | 0.5   | —     | 3.5         | —           | —           |
|     | ferulic acid                                             |                  | —     | —     | —     | —     | 3.5   | —           | —           | —           |
| (d) | Isopropyl lauroyl sarcosinate                            |                  | qsp100| qsp100| qsp100| qsp100| qsp100| qsp100      | qsp100      | qsp100      |
| Photostability | | Sun Test (24 h) | Very Good | Good | Good | Good | Good | Poor | Very Poor | Very Poor |
|     |                                                          | Sun Exposure Test (1 M) | Very Good | Good | Good | Good | Good | Poor | Very Poor | Very Poor |
| Temperature Stability (2 M) | | −5° C. | Very Good | Very Good | Very Good | Very Good | Very Good | Good | Good | Good |
|     |                                                          | 4° C. | Very Good | Very Good | Very Good | Very Good | Very Good | Good | Good | Good |
|     |                                                          | RT | Very Good | Very Good | Very Good | Very Good | Very Good | Poor | Poor | Poor |
|     |                                                          | 50° C. | Very Good | Good | Good | Good | Good | Very Poor | Very Poor | Very Poor |
| Temperature Stability (Cycle: 10 days) | | Cycle (−25° C. to 25° C.) | Good | Good | Very Good | Very Good | Good | Good | Good | Good |

RT: Room Temperature

[Evaluations].
(Photostability)

Each of the compositions according to Examples 1-5 and Comparative Examples 1-3 was filled into a glass bottle and was tested by Sun Test* (24 h) and Sun Exposure Test** (1 month).

Each composition after the above tests was evaluated in accordance with the following criteria.
Very Good: No color change
Good: Little or almost no color change
Poor: Color change
Very Poor: Remarkable color change
*Sun Test
The glass bottle was exposed to artificial sun light by using SUNTEST CPS+ (Atras) under the following conditions.
Irradiance: 765 W/m$^2$
Temperature: 25° C.
Duration of test: 24 hours
**Sun Exposure Test
The glass bottle was exposed to natural sun light for 1 month.
(Temperature Stability)

Each of the compositions according to Examples 1-5 and Comparative Examples 1-3 was filled into a glass bottle and was held under temperature conditions of −5° C., 4° C., room temperature (25° C.) or 50° C. for 2 months, and cycle conditions (−25~25° C.: 10 days).

Each composition after the above tests was evaluated in terms of the degree of change (color, odor, and presence or absence of crystallization) at room temperature in accordance with the following criteria.

Very Poor: Change in color, odor, and presence of crystallization could be remarkably noticed.

The compositions according to Examples 1-5 which included all ingredients (a) to (d) were stable over time even under exposure to light and/or under relatively high temperatures.

The composition according to Comparative Example 1 which lacked ingredient (b) was less stable over time under exposure to light and/or under relatively high temperatures.

The composition according to Comparative Example 2 which lacked ingredient (c) was less stable over time under exposure to light and/or under relatively high temperatures.

It should be remarked as a result of the comparison of the compositions according to Comparative Examples 1 and 2 that the absence of ingredient (c) in the composition according to Comparative Example 2 increased instability due to the exposure to light as compared to the composition according to Comparative Example 1, although ingredient (b) was present in the composition according to Comparative Example 2.

The composition according to Comparative Example 3 which lacked ingredients (b) and (c) was less stable over time under exposure to light and/or under relatively high temperatures.

It should be remarked as a result of the comparison of the compositions according to Comparative Examples 2 and 3 that the presence of ingredient (b) in the composition according to Comparative Example 2 did not affect the photostability due to exposure to light as compared to the composition according to Comparative Example 3 which lacked ingredient (b).

Example 6

The following composition according to Example 6 shown in Table 2 was prepared as a whitening oil stick by mixing the components shown in Table 2. The numerical values for the amounts of the components shown in Table 2 are all based on "% by weight" as active raw materials.

TABLE 2

|  | Example 6 |
| --- | --- |
| Capryloyl Salicylic Acid | 0.15 |
| Pentaerythrityl tetra-di-t-butyl hydroxyhydrocinnamate | 0.1 |
| Phenylethyl resorcinol | 0.3 |
| Isononyl Isononanoate | 20.55 |
| Tridecyl Trimellitate | 18 |
| Hydrogenated Castor Oil Dimer Dilinoleate | 2 |
| Isopropyl Lauroyl Sarcosinate | 6 |
| Dibutyl Ethylhexanoyl Glutamide | 1.3 |
| Dibutyl Lauroyl Glutamide | 2.6 |
| Ethylenediamine/Stearyl Dimer Dilinoleate Copolymer | 17 |
| Hydrogenated Polyisobutene | 18 |
| Hexyldecanol | 12 |

The composition according to Example 6 is in the form of a clear transparent solid stick. The composition according to Example 6 can be used as a whitening product for a keratin substance such as skin.

The composition according to Example 6 is stable over time even under exposure to light and/or under relatively high temperatures.

The invention claimed is:

1. A cosmetic composition, comprising:
   (a) phenylethyl resorcinol;
   (b) at least one lipophilic UV filter selected from drometrizole trisiloxane or bis-ethylhexyloxyphenol methoxyphenyl triazine;
   (c) at least one lipophilic antioxidant selected from pentaerythrityl tetra-di-t-butyl hydroxyhydrocinnamate or ferulic acid; and
   (d) at least one oil selected from the group consisting of diethyl sebacate, isopropyl lauroyl sarcosinate, diisopropyl sebacate, bis(2-ethylhexyl) sebacate, diisopropyl adipate, di-n-propyl adipate, dioctyl adipate, bis(2-ethylhexyl) adipate, diisostearyl adipate, bis(2-ethylhexyl) maleate, triisopropyl citrate, triisocetyl citrate, triisostearyl citrate, glyceryl trilactate, glyceryl trioctanoate, trioctyldodecyl citrate, trioleyl citrate, neopentyl glycol diheptanoate, and diethylene glycol diisononanoate,
   wherein the amount of the (a) phenylethyl resorcinol ranges from 0.2 to 15% by weight, relative to the total weight of the cosmetic composition,
   the amount of the (b) lipophilic UV filter ranges from 3 to 12% by weight, relative to the total weight of the cosmetic composition,
   the amount of the (c) lipophilic antioxidant ranges from 0.1 to 10% by weight, relative to the total weight of the cosmetic composition,
   the amount of the (d) oil ranges from 70 to 90% by weight, relative to the total weight of the cosmetic composition.

2. The cosmetic composition according to claim 1, wherein the cosmetic composition is anhydrous.

3. A cosmetic process for a keratin substance, comprising applying the cosmetic composition according to claim 1 onto the keratin substance.

* * * * *